United States Patent
Sweeney et al.

(10) Patent No.: US 6,723,707 B1
(45) Date of Patent: Apr. 20, 2004

(54) USE OF INSULIN-LIKE GROWTH FACTOR-I IN MUSCLE

(75) Inventors: H. Lee Sweeney, Philadelphia, PA (US); Nadia A. Rosenthal, Concord, MA (US)

(73) Assignees: The Trustees of the University of Pennsylvania, Philadelphia, PA (US); Massachusetts General Hospital, Charlestown, MA (US)

( * ) Notice: Subject to any disclaimer, the term of this patent is extended or adjusted under 35 U.S.C. 154(b) by 0 days.

(21) Appl. No.: 09/510,268

(22) Filed: Feb. 22, 2000

Related U.S. Application Data (63) Continuation of application No. PCT/US98/17428, filed on Aug. 25, 1998.
(60) Provisional application No. 60/057,021, filed on Aug. 25, 1997.

(51) Int. Cl.[7] .................. A01N 43/04; A01N 63/00; A01N 65/00; A61K 31/70; A61K 48/00
(52) U.S. Cl. ................. 514/44; 424/93.1; 424/93.2; 424/93.6; 435/320.1; 435/325; 536/23.5
(58) Field of Search ............... 435/325, 320.1; 536/23.5; 514/44; 424/93.1, 93.2, 93.6

(56) References Cited

U.S. PATENT DOCUMENTS

2003/0018984 A1 * 1/2003 Coleman et al. ............... 800/4

OTHER PUBLICATIONS

Xiao et al. (1996) Efficient long–term gene transfer into muscle tissue of immunocompetent mice by adeno–associated virus vector. J. Virol. 70(11): 8098–8108.*
Allen and Boxhorn., 1989, J. Cell Physiol., 138:311–314.
Barton–Davis et al., 1998, Proc. Natl. Acad. Sci. USA 95:15603–15607.
Barton–Davis et al., 1999, Acta Physiol. Scand 167:301–305.
Benecke et al., 1992, Diabetes 42:206–212.
Brooks and Faulkner, 1988, J. Physiol. 404:71–82.
Carlson and Faulkner, 1983, Med. Sci. Sports Exerc. 15:187–198.
Cohick and Clemmons, 1993, Ann. Rev. Physiol. 55:131–153.
Coleman et al., 1995, J. Biol. Chem. 270:12109–12116.
Donoghue et al., 1988, Genes and Development 2:1779–1790.
Florini and Magri, 1989, Am. J. Physiol. 256:C701–711.
Florini et al., 1996, Endocrine Reviews 17:481–517.
Hogan et al,. 1986, Manipulating the Mouse Embryo: A Laboratory Manual, Cold Spring Harbor, New York (too voluminous to submit).
Juan Li et al., 1996, J. Virol. 70:8098–8108.
Krishan and Dhoot, 1996, J. Muscle Res. and Cell Motility 17:513–521.
Lamberts et al., 1997, Science 278:419–424.
Larrson and Edstrom, 1986, J. Neurol. Sci. 76:69–89.
Leferovich et al., 1995, J. Neurosci. 14:596–603.
Papadakis et al., 1996, Ann. Intern. Med. 124:708–716.
Petrof et al., 1993, Proc. Natl. Acad. Sci. USA 90:3710–3714.
Petrof et al., 1993, Am. J. Physiol. 265, 34:C834–C841.
Rosenthal et al., 1990, Nucl. Acids Res. 18:6239–6245.
Rosenthal et al., 1989, Proc. Natl. Acad. Sci. USA 86:7780–7784.
Samulski et al., 1989, J. Virol. 63:3822–3828.
Sara and Hall, 1986, Physiol. Rev. 70:591–614.
Sartore et al., 1982, Nature 298:294–296.
Schiaffino et al., 1997, In: *Methods in Cell Biology*, pp. 349–367, Emerson and Sweeney, eds., Academic Press, New York.
Shimatsu and Rotwein, 1987, J. Biol. Chem. 262:7894–7900.
Stewart and Rotwein, 1996, Physiol. Reviews 76:1005–1026.
Zdanowicz et al., 1995, Endocrinology 136:4880–4886.

* cited by examiner

*Primary Examiner*—Anne-Marie Falk
(74) *Attorney, Agent, or Firm*—Morgan, Lewis & Bockius, LLP (57) ABSTRACT

The invention relates compositions and method for the use of insulin-like growth factor to enhance muscle mass and strength.

13 Claims, 6 Drawing Sheets

FIG. 1A IGF-1 rAAV Gene Construct

ITR | MLC 1/3 Promoter 1.5 Kb | IGF-1 0.6 Kb | SV40pA 0.85 Kb | MLC Enh 0.9 Kb | ITR

FIG. 1B

IGF-1

FIG. 1C

Actin

FIG. 1D

RNA

FIG. 2B

FIG. 3A Muscle Mass
FIG. 3B Tetanic Force
FIG. 3C Specific Force

FIGURE 4

5'- ggacgtaccaaaatgagcgcacctccaataaagatacacatcatgtcgtcttcacatctcttctacctggcactctgctt
gctcacctttaccagctcggccacagccggaccagagacccttttgcggggctgagctggtggacgctcttcagttcgtgt
gtggaccaaggggcttttacttcaacaagcccacaggctatggctccagcattcggagggcaccacagacgggcattgtg
gatgagtgttgcttccggagctgtgatctgaggaggctggagatgtactgtgctccgctgaagcctacaaagtcagctcg
ttccatccgggcccagcgccacactgacatgcccaagactcagaaggaagtacacttgaagaacacaagtagaggaagtg
caggaaacaagacctacagaatgtaggaggagcctcccgaggaacagaaaatgccacgtcaccgcaagatcctttgctgc
ttgagcaacctgcaaaacatcggaacacctgccaaatatcaataatgagttcaataccatttcagagatgggcatttccc
tcaatgaaatacacaagtaaacattccgacattgtctttaggagtggtttgttaaaaaaaaaaacaaaaaacaaaaacaa
aaacaaaaaaaaagcttgcaccttgcaaaagtggtcctggcgtgggtagattgctgttaatcctttatcaataacgttct
atagagaatatataaatatatatataattatatctcctagtccctgcctcttaagagccgaaaatgcatgggtgttgtag
acattcggttgcactaaattcctctctgaattttggctgctgaagccgttcatttagcaactgtttataggtggttgatg
aatggttccttatctccatttcttcctatgtagcttaagccgcttccttcacagaatctaataatctcgtctaggccatt
agccctgcccttttcttaacattcttgtatttgttgaatttggcctcctcgaaagcaatagcaactgggtggcccacccaa
gttttaacgccc-3'

FIG. 5B
Tg MLC/IGF-I 6 months

FIG. 5A
Wild Type 6 months

USE OF INSULIN-LIKE GROWTH FACTOR-I IN MUSCLE

CROSS REFERENCE TO RELATED APPLICATIONS

This application is a continuation of Application No. PCT/US98/17428 filed Aug. 25, 1998 which claims priority to U.S. Provisional Patent Application No. 60/057,021 filed Aug. 25, 1997.

FIELD OF THE INVENTION

The field of the invention is the use of insulin-like growth factor I to affect vertebrate muscle mass and strength.

BACKGROUND OF THE INVENTION

One of the primary consequences of aging leading to significantly impaired function in the elderly population is the loss of skeletal muscle strength and mass (Lamberts et al., 1997, Science 278:419–424). Both muscle mass and strength decrease by up to one third in humans between the ages of 30 and 80 years (Tzankoff et al., 1977, J. Appl. Physiol. 43:1001–1006). In addition, selective loss of the fastest, most powerful muscle fiber types (type IIb fibers) has been documented (Grimby et al., 1982, Acta Physiol. Scand. 115:125–134). Similar age-related muscle alterations have been observed in rats and mice, indicating that the trend is maintained in other mammalian species (Larrson and Edstrom, 1986, J. Neurol. Sci. 76:69–89; Brooks and Faulkner, 1988, J. Physiol. 404:71–82).

The loss of muscle mass and strength seen in aging mammals has given impetus to the search for compounds which may slow or reverse the process. One such compound is insulin-like growth factor I (IGF-I), which is a peptide growth factor that is structurally related to proinsulin (Cohick et al., 1993, Ann. Rev. Physiol. 55:131–153). IGF-I is critical in mediating the growth of muscle and other tissues (Florini et al., 1996, Endocrine Reviews 17:481–517). Systemic administration of IGF-I results in increased muscle protein content and reduced protein degradation (Zdanowicz et al., 1995, Endocrinology 136:4880–4886). Moreover, over-expression of IGF-I has been correlated with muscle hypertrophy in transgenic mouse lines (Coleman et al., 1995, J. Biol. Chem. 270:12109–12116). Further, addition of IGF-I to cultures of differentiating myocytes has been shown to result in hypertrophied myotubes (Florini et al., 1989, Am. J. Physiol. 256:C701–711).

Previous studies have also suggested that there is a correlation between aging-related loss of muscle mass and strength and decreased levels of IGF-I. Lamberts et a. (1997, Science 278:419–424), demonstrated that with aging, there is a decrease in the production and activity of the growth hormone/IGF-I axis which leads to an increase in catabolic processes as exhibited by the age-related loss of muscle mass and strength. The prevention of muscle mass loss has been achieved in healthy individuals by growth hormone administration, and is associated with increases in IGF-I levels (Papadakis et al., 1996, Ann. Intern. Med. 124:708–716).

The above-stated observations may also have important implications with regard to various muscular diseases. For example, aging-related changes in skeletal muscle mirror the early functional changes observed in muscular dystrophy, albeit on a much slower time scale. Just as in the muscles of old mice, the muscles of the mouse model of Duchenne muscular dystrophy (the mdx mouse) exhibit both decreased force per cross-sectional area and preferential loss of type IIb fibers (Petrof et al., 1993, Am. J. Physiol. 265 (Cell Physiol. 34):C834–C841). These data suggest that IGF-I expression in dystrophic muscle, while not addressing the primary defect that results in increased susceptibility to injury (Petrof et al., 1993, Proc. Natl. Acad. Sci. USA 90:3710–3714), may increase the rate of regeneration of the muscle and thereby tend to preserve muscle function.

Although the previous studies suggested that IGF-I may be useful in preserving muscle mass, these studies failed to demonstrate functional hypertrophy. That is, although there was an increase in muscle mass (i.e., hypertrophy), there was no concomitant increase in specific muscle strength (defined as force per cross-sectional area). For example, Coleman et al. (1995, J. Biol. Chem. 270:12109–12116), demonstrated that the hypertrophic muscles of transgenic mice did not exhibit enhanced strength compared with muscle obtained from nontransgenic, but otherwise identical animals. Indeed, the hypertrophied muscles of transgenic mice, although larger, were actually weaker than their non-transgenic counterparts (Leferovich et al, 1995, J. Neurosci. 14:596–603). Thus, while there are clear indications that IGF-I may be involved in maintaining muscle mass in elderly individuals, these studies did not suggest that muscle function, as measured by strength, may be preserved by the administration of IGF-I.

To date, the only means for stimulating muscle hypertrophy involve the use of steroids which have deleterious side effects. Systemic administration of IGF-I or growth hormone has proved ineffective ans also may have deleterious side effects. Thus, there is a long-felt and unfilled need for the development of compositions and procedures for promoting growth of adult muscle, which growth also serves to enhance the overall strength of the muscle. The present invention satisfies this need.

SUMMARY OF THE INVENTION

The invention relates to a method of increasing vertebrate muscle mass and muscle strength. The method comprises administering a muscle enhancing dose of an isolated nucleic acid encoding Insulin-like Growth Factor I (IGF-I), or a modification or biologically active portion thereof, intramuscularly into a vertebrate, wherein the isolated nucleic acid is expressed in muscle cells, thereby increasing the muscle mass and the muscle strength in the muscle of the vertebrate.

In one aspect, the vertebrate is selected from a group consisting of rat, mouse, cat, dog, horse, cow, pig, sheep, goat, fish, bird, and human.

In a preferred embodiment, the vertebrate is a human.

In another preferred embodiment, the IGF-I is of the same species as the vertebrate.

In another aspect, the isolated nucleic acid is contained within a virus vector.

In yet another aspect, the muscle enhancing dose ranges from between about $10^{10}$ to about $10^{12}$ recombinant virus vector particles per gram of muscle.

In yet another aspect; the method further comprises administering to the vertebrate fibroblast growth factor or neurotropin.

The invention also relates to an isolated nucleic acid comprising a vertebrate IGF-I coding region, or a modification or portion thereof, operably linked to a muscle specific promoter/regulatory region, wherein the IGF-I coding region is flanked on the 5' side by an SV40 intron sequence and wherein the IGF-I coding region is flanked on the 3' end by an SV40 polyadenylation signal sequence.

In one aspect, the muscle specific promoter/regulatory region is selected from a group consisting of the myosin light chain 1/3 promoter/enhancer, the skeletal α-actin promoter, the muscle creatine kinase promoter/enhancer and a muscle specific troponin promoter.

In a preferred embodiment, the muscle specific troponin promoter is the fast troponin C promoter/enhancer.

In another preferred embodiment, the muscle specific promoter/regulatory region is the myosin light chain 1/3 promoter/enhancer.

In another aspect, the muscle specific promoter/regulatory region further comprises an enhancer element operably linked to the IGF-I coding region.

In a preferred embodiment, the enhancer is the myosin light chain 1/3 enhancer.

Also included in the invention is a composition comprising a recombinant virus vector comprising an isolated nucleic acid comprising a vertebrate IGF-I coding region, or a modification or portion thereof, operably linked to a muscle specific promoter/regulatory region, wherein said IGF-I coding region is flanked on the 5' side by an SV40 intron sequence and wherein said IGF-I coding region is flanked on the 3' end by an SV40 polyadenylation signal sequence. The muscle specific promoter/regulatory region further comprises an enhancer element operably linked to the IGF-I coding region and the enhancer is the myosin light chain 1/3 enhancer.

In one aspect, the recombinant virus vector is selected from the group consisting of an adeno-associated virus, an adenovirus and a herpes simplex virus.

In a preferred embodiment, the recombinant virus vector is an adeno-associated virus.

Also included in the invention is a cell comprising an isolated nucleic acid comprising a vertebrate IGF-I coding region, or a modification or portion thereof, operably linked to a muscle specific promoter/regulatory region, wherein said IGF-I coding region is flanked on the 5' side by an SV40intron sequence and wherein said IGF-I coding region is flanked on the 3' end by an SV40 polyadenylation signal sequence.

The invention further includes a cell comprising a recombinant virus vector comprising an isolated nucleic acid comprising a vertebrate IGF-I coding region, or a modification or portion thereof, operably linked to a muscle specific promoter/regulatory region, wherein said IGF-I coding region is flanked on the 5' side by an SV40 intron sequence and wherein said IGF-I coding region is flanked on the 3' end by an SV40 polyadenylation signal sequence. The muscle specific promoter/regulatory region further comprises an enhancer element operably linked to the IGF-I coding region and the enhancer is the myosin light chain 1/3 enhancer.

The invention additionally includes a kit for increasing muscle mass and muscle strength in a vertebrate. The kit comprises a muscle enhancing dose of an isolated nucleic acid comprising a vertebrate IGF-I coding region, or a modification or portion thereof, operably linked to a muscle specific promoter/regulatory region, wherein said IGF-I coding region is flanked on the 5' side by an SV40 intron sequence and wherein said IGF-I coding region is flanked on the 3' end by an SV40 polyadenylation signal sequence, wherein the isolated nucleic acid is expressed in vertebrate muscle cells, and wherein the kit further comprises an applicator for delivering the muscle enhancing dose, and instructions for the use of the kit.

Also included in the invention is a non-human transgenic vertebrate animal comprising an isolated nucleic acid encoding IGF-I, or a modification or biologically active portion thereof.

In one aspect, the IGF-I is operably linked to a muscle specific promoter/regulatory sequence at the 5' end of the IGF-I and a polyadenylation termination signal at the 3' end of the IGF-I.

In another aspect, the muscle specific promoter/regulatory sequence is selected from the group consisting of the myosin light chain 1/3 promoter/enhancer, the skeletal α-actin promoter, the muscle creatine kinase promoter/enhancer and a muscle specific troponin promoter.

In yet another aspect, the non-human transgenic vertebrate animal is selected from the group consisting of rat, mouse, cat, dog, horse, cow, pig, sheep, goat, fish, bird, and human.

BRIEF DESCRIPTION OF THE DRAWINGS

FIG. 1A is a diagram depicting the structure of the IGF-I rAAV construct. Rat IGF-I cDNA was placed under the control of a fast muscle-specific promoter/regulatory sequence (myosin light chain 1/3 termed "MLC 1/3") positioned at the 5' end of the IGF-I cDNA. A SV40 polyadenylation sequence (SV40pA) was positioned at the 3' end of the IGF-I cDNA. On the 3' end of the SV40pA sequence, the MLC 1/3 enhancer sequence was inserted into the construct. The gene construct was then inserted into a rAAV transfer plasmid (pSUB201) between the inverted terminal repeat sequences (ITRs) of the virus.

DETAILED DESCRIPTION OF THE INVENTION

It has been discovered in the present invention that introduction of an isolated nucleic acid encoding IGF-I into adult muscle cells, wherein IGF-I is then expressed in the adult muscle cells, results in hypertrophy of the muscle and/or reversal of age-related muscular atrophy. More importantly, in contrast to prior art procedures, the overall strength of the muscle is enhanced. Without wishing to be bound by theory, it may be that recombinant virus-mediated muscle fiber expression of IGF-I activates satellite cells where prior art methods failed to do so in that prior art procedures did not sufficiently elevate local levels of IGF-I in the muscle. Alternatively, it may be that systemic IGF-I failed to gain access into and to activate satellite cells. In any event, the present invention has circumvented the obstacles which prior art compositions and procedures failed to overcome.

Senescence in mammals is accompanied by loss of strength and endurance in the skeletal musculature. This is due, inter alia, to a diminution in the average diameter of muscle fibers, a shift to less powerful muscle fiber types, decreased mitochondrial volume, and decreased mitochondrial efficiency. The most significant loss of muscle mass in adult muscle is due to the reduction in the number and/or size of the largest, most powerful muscle fibers, the type IIb and type IIx fibers.

The invention relates to the introduction of IGF-I into adult muscle. In a preferred embodiment, a recombinant viral vector delivery system, i.e., an adeno-associated viral (AAV) vector, was used to introduce nucleic acid encoding IGF-I into the muscle tissue of a mammal. However, the invention should not be construed to be limited to any particular vector or to any particular strain of AAV. Rather, the invention should be construed to include all other means of introducing nucleic acid encoding IGF-I into muscle cells including, but not limited to, any strain of AAV which is capable of delivering genes to muscles cells (for example, including, but not limited to, AAV- 1, AAV-3, AAV-4 and AAV-6), other viruses including adenoviruses, herpes simplex viruses, retroviruses, and the like. The invention also includes plasmid-based delivery vectors as well as the administration of DNA in the absence of any vector such as administration of naked DNA by a "gene gun" approach, or the administration of coated DNA, or any other method facilitating DNA entry into muscle tissue.

By the term "naked DNA" as used herein, is meant DNA, which, irrespective of the route or method of administration, is administered to an animal in the absence of any substantial amount of protein, lipid, or any other compound either covalently bound to or non-covalently associated with the DNA. For example, naked DNA includes but is not limited to a plasmid or an isolated nucleic acid fragment encoding a sequence of interest whether naturally or synthetically derived.

An "isolated nucleic acid," as the term is used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "substantially purified" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The term "coated DNA," as used herein, describes a DNA associated with a non-proteinaceous substance which may be administered to an animal. Such non-proteinaceous substances include but are not limited to lipids, polylysine, glycosylated polylysine, and the like.

In a preferred embodiment, the IGF-I coding sequence used in the compositions and methods of the invention is the 0.6 kb rat IGF-I cDNA. The invention, however, is not limited solely to this IGF-I DNA. Instead, the invention encompasses any and all IGF-I coding sequences having the biological activity of IGF-I including promoting muscular hypertrophy and enhancing muscle strength as described herein. For example, the invention should be construed to include all mammalian IGF-I sequences which are either known or unknown. The preferred type of IGF-I to be used depends upon the species of animal being treated, in that, the it is preferred that the IGF-I be species matched. Thus, for example, when a human is being treated, the preferred type of IGF-I is human IGF-I, etc. Although all forms of IGF-I are likely to have an effect in different animals, species matching will void potential adverse immunological complications stemming from the induction of an immune response to an IGF-I of a different species in any given animal. Sources of IGF-I from different animal species include the following types of IGF-I and accompanying GenBank Accession Numbers: Cervus elaphus insulin-like growth factor I (IGF4) mRNA, Accession No. U62106; Equus caballus insulin-like growth factor I precursor (IGF-I) mRNA, Accession No. U28070; Goat mRNA for insulin-like growth factor-I, Accession No. D11378; Oryctolagus cuniculus insulin-like growth factor I precursor (IGF-I) mRNA, Accession No. U75390; Pig insulin-like growth factor I (pIGF-I) mRNA, Accession No. M31175; Ovis aries insulin-like growth factor I (IGF-I) mRNA, Accession No. M89787; Human insulin-like growth factor (IGF-I) IA and IB gene, exon 1, Accession Nos. M12659, M77496; Rat insulin-like growth factor I (IGF-I) mRNA, Accession No. M15480; Chicken insulin-like growth factor (IGF-I) mRNA, Accession Nos. M3279 1, M29720; Salmon insulin-like growth factor I (IGF-I) mRNA, M32792; X. laevis insulin-like growth factor I (IGF-I) mRNA, Accession No. M29857. Thus, the invention should be construed to include DNA encoding IGF-I, or a biologically active portion thereof, from humans and non-human mammals, including but not limited to mouse, human, cow, pig, horse, sheep, rat, goat, Xenopus, and the like, which IGF-I functions in a substantially similar manner to the rat IGF-I described herein. Furthermore, IGF-I is thought to serve a similar role in other vertebrates as it does in mammals. Thus, transgenic fish or birds having and expressing IGF-I in mature muscle fibers (i.e., via the use of muscle specific promoters) will result in increased muscle mass in juvenile and adult animals. In preliminary experiments using bird muscle cells in vitro, it is evident that IGF-I has an effect on these cells, which effect is predictive that treatment of avian, fish and other muscle cells with the appropriate IGF-I will serve to increase the mass and strength of muscle tissue in these animals.

The term "non-human transgenic vertebrate animal" as used herein means an animal, the somatic and germ cells of which comprise an isolated nucleic acid comprising IGF-I.

Preferably, the nucleotide sequence comprising the gene encoding IGF-I is about 50% homologous, more preferably about 70% homologous, even more preferably about 80% homologous and most preferably about 90% homologous to the gene encoding human IGF-I and whose sequence is provided in (1986, J. Biol. Chem. 261:4828–4832). It should be noted that alternative RNA processing in the cell results in the production of two IGF-I precursor polypeptides and that both forms work in the experiments described herein. In addition, IGF-I obtained form rat liver or muscle may be used for comparison (1987, Mol. Endocrinol. 1:243–248).

The use of the term "DNA encoding" should be construed to include the DNA sequence which encodes the desired protein and any necessary 5' or 3' untranslated regions accompanying the actual coding sequence.

The term "expression of a nucleic acid" as used herein means the synthesis of the protein product encoded by the nucleic acid.

By "biologically active" as used herein, is meant an IGF-I protein, or any portion, modification or variant thereof, which is capable of mediating a substantially similar increase in and/or prevention of the loss of muscle mass and specific muscle strength as demonstrated for rat IGF-I as measured by the methods described herein.

By the term "specific strength," as used herein, is meant the force generated by a muscle divided by its cross-sectional area as determined pursuant to the methods described by Brooks and Faulkner (1988, J. Physiol. 404:71–82).

The invention should also be construed to include DNA encoding variants of IGF-I which retain IGF-I biological activity as defined previously herein. Such variants, i.e., analogs of proteins or polypeptides of IGF-I, include proteins or polypeptides which have been or may be modified using recombinant DNA technology such that the protein or polypeptide possesses additional properties which enhance its suitability for use in the methods described herein, for example, but not limited to, variants conferring enhanced stability on the protein in muscle, enhanced specific activity of the protein, and increased ability of the protein to remain localized in muscle tissues. Analogs can differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;

valine, isoleucine, leucine;

aspartic acid, glutaric acid;

asparagine, glutamine;

serine, threonine;

lysine, arginine;

phenylalanine, tyrosine.

Preferably, the amino acid sequence of an IGF-I analog is about 70% homologous, more preferably about 80% homologous, even more preferably about 90% homologous, more preferably, about 95% homologous, and most preferably, at least about 99% homologous to the amino acid sequence of IGF-I described in (1986, J. Biol. Chem. 261:4828–4832) and in (1987, Mol. Endocrinol. 1:243–248).

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

Any number of procedures may be used for the generation of mutant or variant forms of IGF-I. For example, generation of mutant forms of IGF-I which do not circulate in the plasma of rAAV-IGF-I-injected animals may be accomplished by introducing deletion, substitution or insertion mutations into an IGF-I encoding nucleic acid residing on a plasmid template using ordinary recombinant DNA methodology described in any molecular biology manual, for example, methods described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). Mutant IGF-I so generated is expressed and the resulting protein is assessed for its ability to remain localized in the muscle as demonstrated by a lack of significant increase in plasma levels of IGF-I such as that described herein. Mutant proteins which appear to be localized to the muscle tissues are then tested for IGF-I biological activity as defined herein. DNA encoding a mutated IGF-I protein which does not cause a significant rise in IGF-I plasma levels but which retains IGF-I biological activity, is suitable for use in the rAAV vector of the invention.

Procedures for the introduction of amino acid changes in a protein or polypeptide by altering the DNA sequence encoding the polypeptide are well known in the art and are also described in Sambrook et al, supra, and Ausubel et al., supra.

It is desirable but not essential that the nucleic acid encoding IGF-I which is introduced into muscle cells in a mammal be expressed and that the protein remain localized within the muscle tissue. This is because if higher than physiologically normal amounts of IGF-I enter the circulatory system, IGF-I may promote undesired growth of other cells which may result in detrimental rather than beneficial effects to the mammal into which IGF-I has been introduced. Thus, the present invention also relates to the use of a truncated form of IGF-I which prevents egress of IGF-I from the muscle tissue into the circulatory system. Such a truncated form is described, for example, in Sara et al. (1986, Physiol. Rev. 70:591–614), wherein there is disclosed a truncated form of IGF-I which is missing the three terminal amino acids in the mature IGF-I peptide.

Accordingly, in a preferred embodiment, the nucleic acid encoding IGF-I introduced into the muscle cells encodes a truncated version of IGF-I which is expressed therefrom. The truncated version of the full-length rat IGF-I cDNA disclosed herein is preferably missing the three terminal amino acids in the mature IGF-I peptide. Expression in muscle of the truncated version does not cause measurable increase in plasma levels of IGF-I in mice as detected by standard methods as set forth herein.

In a preferred embodiment, the invention relates to the use of a muscle specific promoter/regulatory region, i.e., the MLC 1/3 promoter, such that DNA encoding IGF-I operably linked to the promoter/regulatory region is expressed at highest levels in type IIb/x fibers. However, the invention is not limited to the use of this or any other particular promoter/regulatory region to drive expression of the DNA encoding IGF-I. Indeed, other promoter/regulatory regions capable of driving expression of a heterologous gene to high levels in muscle cells, more desirably, in type IIb/x muscle cells, include, but are not limited to, the skeletal α-actin promoter and the muscle creatine kinase promoter/enhancer, and the like. Other muscle specific promoters may be used, including the skeletal muscle troponin subunit promoter, such as the fast troponin C promoter/enhancer sequence. It is important to note that it is preferable to use a muscle specific promoter when administering IGF-I to an animal, although it is possible to use a variety of non-muscle specific promoters as well, including constitutive promoters such as viral promoters. However, when the invention includes expression of IGF-I in a transgenic animal, a muscle specific promoter is the promoter of choice, in order to avoid any potential deleterious side effects which may arise as a result of expression of IGF-I in non-muscle tissue.

In another preferred embodiment, the rAAV-IGF-I recombinant of the invention comprises several DNA elements. These DNA elements include at least two copies of an AAV inverted terminal repeat (ITR) sequence, a 1.5 kb MLC 1/3 promoter/regulatory element previously discussed herein, a 0.85 kb SV40 polyadenylation sequence signal, and a 0.9 kb MLC 1/3 enhancer element, all operably linked to the IGF-I DNA coding region, as well as any necessary 5' or 3' untranslated regions which flank the DNA encoding IGF-I. However, the invention should not be interpreted as being limited to the presence of any or all of these particular elements or to any particular arrangement thereof. Rather, the invention encompasses other promoter/regulatory regions, enhancers, polyadenylation signal sequences, and the like, arranged in various orders and permutations thereof. Further, the invention includes constructs which do not have one or more of the above-stated DNA elements.

As used herein, the term "promoter/regulatory sequence" means a DNA sequence which is required for expression of a gene operably linked to the promoter/regulatory sequence. In some instances, this sequence may be the core promoter sequence and in other instances, this sequence may also include an enhancer sequence and other regulatory elements which are required for expression of the gene in an inducible/repressible or tissue-specific manner.

By describing two nucleic acids as being "operably linked" as used herein, is meant that a single-stranded or double-stranded nucleic acid comprises each of the two nucleic acids and that the two nucleic acids are arranged within the nucleic acid in such a manner that at least one of the nucleic acid sequences is able to exert a physiological effect by which it is characterized upon the other.

By the term "positioned at the 5' end" as used herein, is meant that the promoter/regulatory sequence is covalently bound to the 5' end of the gene whose expression it regulates, at a position sufficiently close to the 5' start site of transcription of the gene so as to drive expression of the gene.

The rAAV vector of the invention also comprises 5' and 3' untranslated regions of DNA which flank the 0.6 kb rat IGF-I cDNA sequence. In the rAAV-IGF-I vector exemplified in the experimental examples section, the 5' untranslated region flanking the IGF-I sequences is as follows: At the 5' end of the IGF-I sequences, the 1.5 kb MLC 1/3 promoter sequence.

A first region of an oligonucleotide "flanks" a second region of the oligonucleotide if the two regions are adjacent one another or if the two regions are separated by no more than about 1000 nucleotide residues, and preferably no more than about 100 nucleotide residues.

In the rAAV-IGF-I vector exemplified in the experimental details section, the 3' untranslated region flanking the IGF-I sequences is as follows: At the end of the translation stop signal, is the 0.85 kb SV40 poly A signal sequence which is followed by the 0.9 kb MLC 1/3 enhancer sequence.

It will be appreciated that other 5' and 3' untranslated regions of DNA may be used in place of those recited in the case of IGF-I.

The rAAV vector of the invention also comprises a transcription termination signal. While any transcription termination signal may be included in the vector of the invention, preferably, the transcription termination signal is the SV40 transcription termination signal.

In a preferred embodiment, a muscle enhancing dose of about $10^{10}$ plaque-forming units (pfu) of rAAV-IGF-I recombinant was administered to the muscle tissue of mice.

By the term "muscle enhancing dose" as the term is used herein, is meant a dose of an isolated nucleic acid, preferably but not necessarily in a recombinant virus vector, wherein the isolated nucleic acid encodes a mammalian IGF-I gene, wherein the isolated nucleic acid is administered to a muscle and IGF-I expressed therefrom induces an increase in muscle size and muscle strength compared with muscle to which an isolated nucleic acid is not administered or with a muscle to which a similar isolated nucleic acid dose is administered which either does not encode or does not express IGF-I.

By the term "administered" as used herein, is meant any method for the introduction of an isolated nucleic acid into muscle tissue. One preferred method is injection of the nucleic acid, or a recombinant vector comprising the nucleic acid either directly into the muscle or into the interstitial space surrounding the muscle of a vertebrate animal. Alternatively, systemic delivery of viral vectors or any other means by which isolated nucleic acid can be introduced into muscle cells including "gene gun", liposomes, and the like are also included in the invention.

The invention is not limited solely to the delivery of factors for the treatment of aging-associated loss of muscle mass and function. Rather, the invention should be construed to include a variety of vectors encoding other muscle enhancing factors for the treatment of various muscle disorders or conditions, which factors may be delivered using the methods of the present invention to the muscle cells of a mammal. Thus, the invention should be construed to include delivery of fibroblast growth factor, neurotrophins, and the like, in combination with IGF-I, or delivery of IGF-I alone to vertebrates.

The invention should also be construed to include nucleic acids encoding various proteins which are useful for the treatment of other muscle associated disease states in a mammal. Such muscle associated disease states include, but are not limited to, Becker muscular dystrophy, Duchenne muscular dystrophy, Limb Girdle muscular dystrophy, facioscapulohumeral dystrophy, spinal muscular dystrophy and amyotrophic lateral sclerosis.

By "therapeutic effect" as used herein as it relates to IGF-I, is meant any increase in muscle mass and muscle strength and/or prevention of loss of muscle mass and muscle strength caused by senescence, disease, weightlessness, or any other condition which causes decrease in muscle mass or strength.

According to the invention, it has been discovered that a preparation of an rAAV vector comprising nucleic acid encoding IGF-I injected into the muscle tissue of an animal at a single site per dose increases muscle mass and strength in young animals and prevents loss of muscle mass and strength in old animals. However, the invention is not limited to this injection regimen. Rather, treatment regimens which are contemplated include a single dose or dosage which is administered hourly, daily, weekly or monthly, or yearly.

The route of administration of the vaccine may also vary depending upon the disorder to be treated.

Typically, the number of viral vector genomes per gram of muscle which are administered in a single injection ranges from about $10^9$ to about $10^{13}$. More preferably, the number of viral vector genomes/mammal which are administered in a single injection is about $2 \times 10^{10}$ viral genomes per gram of muscle.

When the method of the invention comprises multiple site simultaneous injections, or several multiple site injections comprising injections into different muscle sites over a period of several hours (for example, from about less than one hour to about two or three hours), the total number of viral vector genomes administered is identical to that recited in the single site injection method.

For administration of the rAAV vector of the invention in a single site injection, a suspension of virus is injected directly into the muscle. For multiple site injection, a needle is inserted into the muscle tissue of the mammal. The vector is injected essentially continuously along the needle track so that a series of intramuscular sites are injected with each injection, each site therefore being at a position further into the muscle tissue than the previous site. Each injection targets from about 5 to about 30 sites along the needle track and patients may receive about 50 total injections. The procedure is therefore akin to an acupuncture procedure which is preferably carried out under anesthesia.

Multiple site injection of rAAV may also be accomplished using a multiple injection device such as that commonly used for the detection of tuberculosis infection.

In a preferred embodiment, the rAAV-IGF-I vector is suspended in a solution of 10% glycerol/HBS. However, the invention is not limited to this formulation. Rather, for administration to the mammal, the rAAV vector comprising IGF-I may be suspended in any pharmaceutically acceptable carrier, for example, HEPES buffered saline at a pH of about 7.8. Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

The rAAV vector of the invention may also be provided in the form of a kit, the kit comprising, for example, a freeze-dried preparation of vector in a dried salts formulation, sterile water for suspension of the vector/salts composition and instructions for suspension of the vector and administration of the same to the mammal.

Thus, included in the invention is a kit for enhancing or preventing the loss of muscle mass and strength. The kit comprises a muscle enhancing dose of an isolated nucleic acid encoding an IGF-I, or a biologically active portion thereof, and/or a recombinant vector comprising the nucleic acid, and an applicator for administering the nucleic acid to muscles, and instructions for using the kit. The instructions for using the kit depend on the particular human or veterinary patient for which the kit is to be used and the target muscle site(s).

In a preferred embodiment, the instructions comprise directions on how to administer a rAAV-IGF-I recombinant to the hind limb of mice. These instructions simply embody the examples provided herein.

The kit may also include instructions on how to administer the rAAV-IGF-I recombinant using the applicator provided therewith.

By the term "applicator" as the term is used herein, is meant any device including but not limited to a hypodermic syringe, a gene gun, and the like, for administering the DNA encoding IGF-I, or a biologically active portion thereof, into the muscles of a human or veterinary patient.

The compositions and methods described herein have the following applications. Muscle strength in aging humans may be preserved and/or enhanced; injured muscle may be caused to heal more effectively and more rapidly; muscle mass may be controlled during disease and/or during prolonged stays in reduced gravity environments; cosmetic body sculpting may be possible by promoting muscle hypertrophy in selected muscle tissue; muscle growth in young animals may be enhanced; muscle mass in adult animals may be enhanced; and, in diabetes, the compositions and methods may be useful for the promotion of glucose clearance from the muscle tissue.

IGF-I is also known to promote glucose uptake in skeletal muscle in an insulin-independent manner, and thus, also be of use in controlling blood glucose levels in diabetics.

In addition as noted herein, the invention includes a non-human transgenic vertebrate animal comprising an isolated nucleic acid comprising IGF-I, which IGF-I is preferably operably linked to a muscle specific promoter/regulatory region at its 5' end, and also comprises a polyadenylation signal at its 3' end. Such non-human transgenic vertebrate animals are expected to comprise up to or even more than 50% more muscle mass than their otherwise identical non-transgenic counterparts. In addition, the muscle mass of the transgenic animal progresses much faster than that of an otherwise identical non-transgenic counterpart animal. Thus, when used as a source of food, the transgenic animal of the invention may be brought to market faster than the non-transgenic counterpart animal. The generation of transgenic animals is well known in the art and is described, for example, in Hogan et al. (1986, Manipulating the Mouse Embryo: A Laboratory Manual, Cold Spring Harbor, N.Y.).

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Expression of Exogenous IGF-I in Muscle Induces Hypertrophy and Increased Muscle Strength in Young Animals and Prevents Loss of Muscle Mass and Function in Older Animals The experiments presented in this example may be summarized as follows.

The data presented herein demonstrate that exogenous production of IGF-I in mammalian muscle increases both muscle mass and muscle strength in young animals and prevents the loss of muscle mass and muscle function in older animals. More specifically, a recombinant adeno-associated virus (rAAV) vector expressing high levels of IGF-I under the control of the MLC 1/3 promoter/enhancer sequence was injected into the right hindlimb muscle of either young (i.e., 2 months of age) or old (i.e., 18 or 24 months of age) mice. The muscle was examined to determine its mass and function at 4 or 9 months after viral injection. In young mice examined at 6 months of age after viral administration at 2 months, the muscle exhibited a 15% increase in mass with a concomitant increase of 14% in isometric force.

The results obtained in old mice where muscles were injected with rAAV-IGF-I were even more remarkable that those observed in young mice. In old mice, the data obtained therefrom demonstrated an increase in muscle mass of 19% compared with the control, non-injected muscle; therefore, the normal 15% decrease in muscle mass normally associated with aging in mice was completely prevented.

Functionally, the rAAV-IGF-I-injected muscle of old mice exhibited increased force relative to control contralateral muscles which was even greater than the increase in cross sectional area thereby completely preventing the loss of specific force (defined as force per cross-sectional area) typically seen in aging skeletal muscle in mice. Further, the rAAV-IGF-I-injected muscle demonstrated specific preservation of the most powerful and fastest muscle fibers, type IIb fibers, normally lost in aging muscle. The selective preservation of type IIb fibers may explain the preservation of specific force observed in rAAV-IGF-I-injected muscle of old mice compared with control muscle of old mice which generated less force per cross-sectional area when compared to the muscles of young mice.

It has therefore been discovered that injection of a rAAV expressing high levels of IGF-I in differentiated muscle fibers, promotes an average increase of 15% in muscle mass and a 14% increase in muscle strength in young adult mice. Even more remarkably, rAAV-IGF-I injection prevents aging-related muscle changes in old adult mice, resulting in a 19% increase in muscle mass and a 27% increase in specific strength compared with uninjected muscles in old mice. Further, rAAV-IGF-I-injected muscles of old mice demonstrated that muscle mass and fiber types were maintained at levels similar to those observed in control, young adult muscles.

Without wishing to be bound by theory, it may be that these effects observed in muscles injected with rAAV-IGF-I recombinant virus are primarily due to stimulation of muscle regeneration by IGF-I which is expressed locally within the muscle, and that the primary cause of aging-related impairment of muscle function is a cumulative failure to repair damage sustained during muscle utilization which repair is somehow mediated by IGF-I. The results disclosed herein suggest that gene transfer of IGF-I into muscle may be an effective human gene therapy for preventing the loss of muscle function associated with aging, and may be of benefit in diseases or conditions where there is loss of muscle mass and/or muscle strength. Such conditions or diseases include, but are not limited to, loss of muscle strength in aging humans; treatment of injured muscle; muscle atrophy caused by disease and/or reduced gravity environments; cosmetic body sculpting including repair of damaged muscle following injury; inducing muscle growth in young animals; increasing muscle mass and strength in adult animals; and promotion of glucose clearance from the muscle tissue in diabetics. In addition, the viral delivery of IGF-I may have therapeutic value in the several diseases, including, but not necessarily limited to, Becker muscular dystrophy, Duchenne muscular dystrophy, Limb Girdle muscular dystrophy, facioscapulohumeral dystrophy, spinal muscular dystrophy and amyotrophic lateral sclerosis.

The Materials and Methods used in the experiments presented in this example are now described.

Viral Construct

Figure 1A:
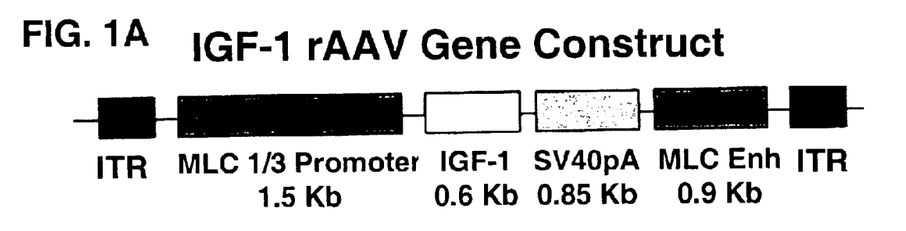

FIG. 1A depicts a schematic diagram of the IGF-I construct. An AAV transfer plasmid (pSUB201) was constructed which contained a myosin light chain (MLC) 1/3 promoter/regulatory sequence, which is known to drive expression of target genes operably linked to the sequence, in differentiated fast-twitch muscle fibers (Allen et al., 1989, J. Cell Physiol., 138:311–314). Rat IGF-I cDNA (Shimatsu et al, 1987, J. Biol. Chem. 262:7894–7900) was inserted into pSUB201 and was operably linked to the MLC 1/3 promoter/regulatory sequence. This promoter/regulatory sequence comprises a 1500 bp MLC1 promoter fragment placed upstream and a 920 bp MLC enhancer fragment placed downstream of the IGF-I transcription cassette. The MLC promoter/regulatory regions were chosen because they have been reported to activate transgene expression in the correct developmental time frame (E9.5) in the mouse and to drive transgene expression to consistently high levels exclusively in adult skeletal muscle (Donoghue et al., 1988, Genes and Development 2:1779–1790; Rosenthal et al., 1989, Proc. Natl. Acad. Sci. USA 86:7780–7784; Rosenthal et al, 1990, Nucl. Acids Res. 18:6239–6245; Benecke et al., 1992, Diabetes 42:206–212).

Figure 4:
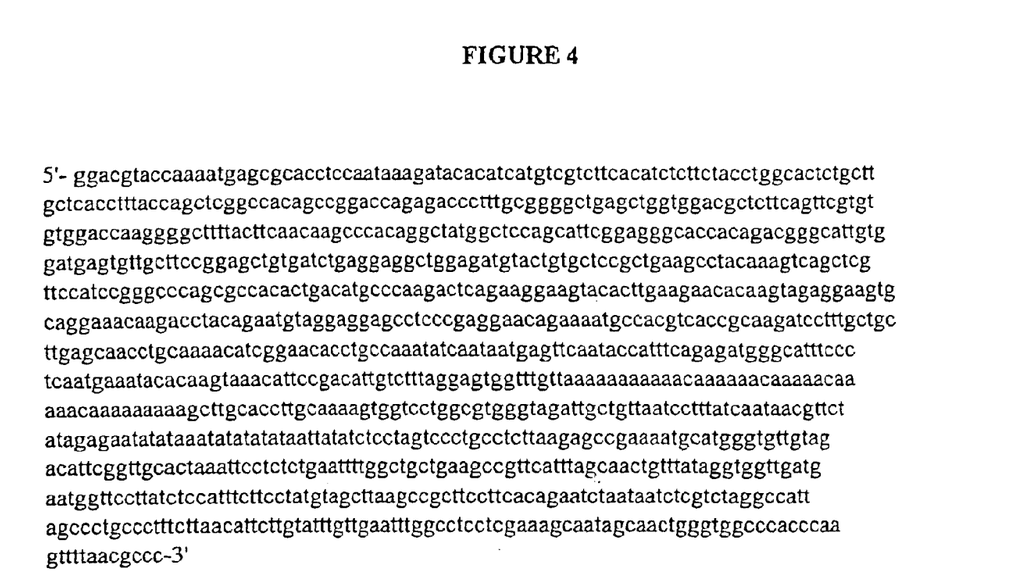
FIG. 4 is the nucleotide sequence of the rat liver form of IGF-I (SEQ ID NO:3).

The coding sequence of a rat liver form of IGF-I, as disclosed by Shimatsu et al. (1987, J. Biol. Chem. 262:7894–7900) was ligated to a SV40-derived intron and a SV40 polyadenylation site was placed downstream of the coding sequences for optimal RNA processing and stability. The DNA sequence is SEQ ID NO:3 as shown in FIG. 4.

The IGF-I cDNA sequences were placed under the control of a dual promoter/enhancer combination sequence derived from the rat MLC 1/3 locus. The entire cassette was then cloned into the AAV vector genome between the AAV ITRs (FIG. 1A) and a recombinant AAV was prepared by the University of North Carolina Gene Therapy Vector Core (Chapel Hill, N.C.), following published procedures (Snider et al, 1996, In: *Current Protocols in Human Genetics* pp. 12.1.1–12.1.24, John Wiley and Sons Press, New York; Juan Li et al., 1996, J. Virol. 70:8098–8108; Samulski et al, 1989, J. Virol. 63:3822–3828).

Injections

Anesthetized C57BL/6 mice of 2, 18, and 24 months of age were injected with 50 μl of 10% glycerol/HBS containing approximately $10^{10}$ rAAV particles (Donoghue et al., 1988, Genes & Development 2:1779–1790) into the interstitial space surrounding the anterior muscles of the right hind limb, which included the extensor digitorum longus (EDL). Briefly, the virus was administered to the mice by injection into the area beneath the connective tissue sheath overlying the targeted muscle using a glass micropipette and a pressure delivery device, or by using a 30 gauge needle. Once the mice regained consciousness, they were returned to the animal facility until further study.

Mechanical Measurements

Approximately 4 or 9 months after viral injection, the mice were sacrificed by cervical dislocation under anesthesia, and the EDL muscles were removed to determine isolated muscle force measurements. The tendons were attached to a rigid post and to an isometric force transducer in a bath of Ringers solution which was gas-equilibrated with 95% $O_2$/5% $CO_2$. The optimum length of the muscle was determined by twitch force from supramaximal stimulation. Maximal tetanic force was determined using a 120 Hz–500 msec pulse which was delivered via two parallel platinum plate electrodes. After the force measurements were completed, the muscles were removed from the bath, blotted to remove excess moisture, and weighed. The muscles were then pinned at optimum length, surrounded by embedding compound (TissueTek), and rapidly frozen in melting isopentane. Muscles were stored at −80° C. until subsequent analysis.

Histology

All muscle tissues were prepared and stained with hematoxylin and eosin as described by Carson (1997, In: *Histotechnology*. American Society of Clinical Pathologists, Chicago).

Detection of Transgene Expression

RT-PCR was performed to detect the presence of IGF-I transcripts in injected muscles. The recombinant DNA methods used are well-known in the art and have been described previously (Sambrook et al., 1989, *Molecular Cloning: A Laboratory Manual*, Cold Spring Harbor Laboratory Press, New York; Ausubel et al., 1997, *Current Protocols in Molecular Biology*, Green & Wiley, New York). Briefly, total RNA isolated from frozen tissue (RNAqueous, Ambion, Austin, Tex.) was subject to reverse transcription and PCR (Perkin Elmer, Calif.) using oligonucleotides specific for rat IGF-I (TGCTCACCTTTACCAGCTCGG [SEQ ID NO: 1], sense primer; GCCCGGATGGAACGAGCT-GACT [SEQ. ID NO: 2], antisense primer). The primers which amplified β cytoplasmic actin (Clontech, Calif.) served as a positive control for the procedure.

Myosin Heavy Chain Composition

Immunohistochemistry was performed to determine neonatal and type IIb myosin heavy chain composition in EDL muscles (Schiaffino et al., 1997, In: *Methods in Cell Biology*, pp. 349–367, Emerson and Sweeney, eds., Academic Press, New York). Primary antibody dilutions used were as follows: Type I myosin (BA-F8), 1:50; Type [IIa myosin (SC-71), 1:10; Type IIb myosin (BF-F3), 1:3; Neonatal myosin (BF-34), 1:10. AMCA-conjugated, goat anti-mouse IgM antibodies and donkey anti-mouse IgG (H+L) (Jackson ImmunoResearch Laboratories, Inc. (West grove, Pa.)) were used as secondary antibodies. Microscopy was performed using a Leitz DMR microscope (Leica, Inc. Exton, Pa.). Image acquisition and analysis was carried out using a MicroMAX digital camera system (Princeton Instruments, Trenton, N.J.) and imaging software (IPLAB, Signal Analytics, Vienna, Va.).

The Results of the experiments presented in this example are now described.

Figure 1B:
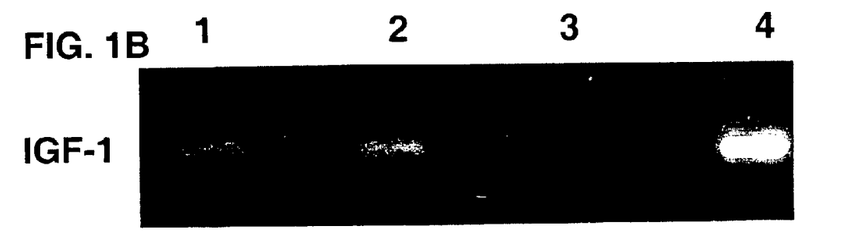
FIG. 1B, comprising three panels, is an image of a gel depicting the persistence of IGF-I expression in muscle following injection therein with rAAV-IGF-I wherein IGF-I expression was detected by reverse-transcriptase polymerase chain reaction (RT-PCR) assay. The lanes were loaded with sample RT-PCR reactions performed on nucleic acid obtained from the following muscle tissues: Lane 1, 27-month-old extensor digitorum longus (EDL) 9 months post-rAAV-IGF-I injection; lane 2, 6-month-old EDL at 4 months post-rAAV-IGF-I injection; lane 3, uninjected age-matched control EDL; lane 4, positive control using the rAA-IGF-I gene construct depicted in FIG. 1A. The expression of IGF-I in the various muscle tissues compared to the positive control in lane 4 is depicted in the top panel of FIG. 1B. The constitutive expression of β-cytoplasmic actin in EDL is depicted in the middle panel of FIG. 1B. In this panel, lanes 1–3 were loaded as described previously. Lane 4 is a positive control using a template supplied with oligonucleotides obtained from Clontech Laboratories, Inc. (Palo Alto, Calif.). In the bottom panel of FIG. 1B, data demonstrating the integrity of RNA isolated from EDL muscles which was analyzed as described in the top and middle panels is shown. Equal volume RNA samples were electrophoresed through a non-denaturing agarose gel (Invitrogen, Carlsbad, Calif.). Lanes 1–3 were loaded as described previously herein.
Figure 1C:
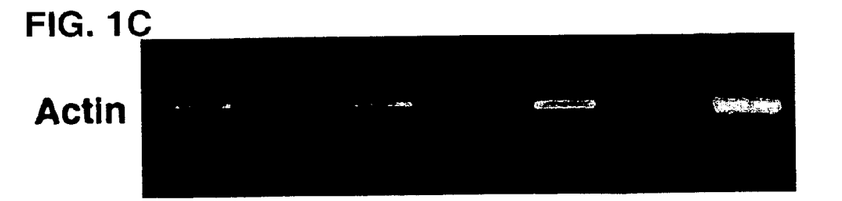
Figure 1D:
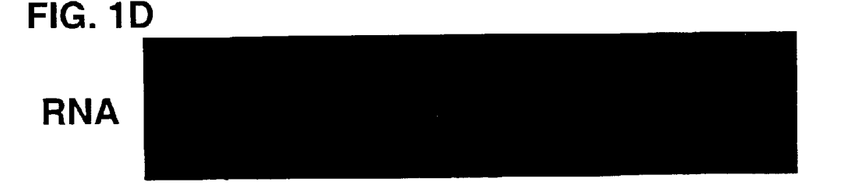

Injection of rAAV Expressing IGF-I Into Muscles of Young Mice Induces Increase in Both Muscle Mass and Muscle Strength and Prevents Loss of Muscle Mass and Force in Old Mice FIG. 1B illustrates expression of the viral driven IGF-I mRNA resulting from direct muscle injection of the rAAV-IGF-I construct the structure of which is shown schematically in FIG. 1A. The IGF-I expression persisted for as long a period as was examined; for mice examined at 27 months of age, following rAAV-IGF-I injection at 18 months of age, this represents 9 months of continued expression.

Figure 2:
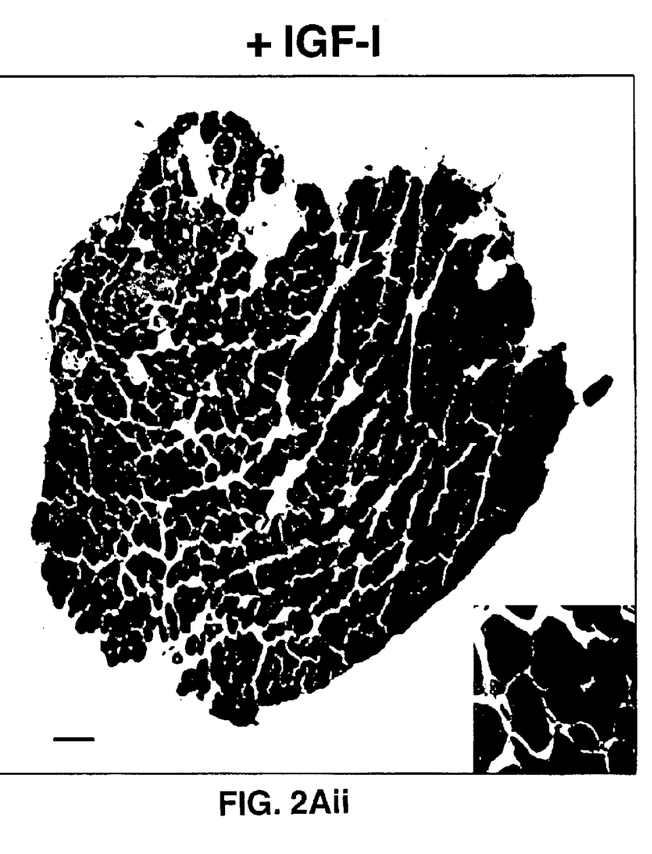
FIG. 2A, comprising two panels, is an image of photomicrographs depicting the effect of IGF-I expression in EDL muscles of young (6 month old) mice 4 months post-rAAV-IGF-I injection. Cross-sections of control non-injected and rAAV-IGF-I-injected EDL muscles were stained with hemotoxilin and eosin. rAAV-IGF-I-injected EDL ("Injected" panel) displayed significant increase in cross-sectional area compared with contralateral non-injected EDL ("Control" panel). Muscle fiber regeneration was evident in rAAV-IGF-I-injected EDL as demonstrated by the presence of central nuclei (insert, "Injected" panel) which were absent in non-injected EDL muscle (insert, "Control" panel). Scale bars equal 100 μm.
FIG. 2B is a graph depicting the effect of IGF-I expression on muscle mass and force generation. Muscle mass (wet weight) and isometric tetanic force of rAAV-IGF-I-injected muscles were expressed relative to the same measurements in the contralateral non-injected muscles. The symbol "*" denotes p<0.05 for paired comparisons between rAAV-IGF-I-injected and control muscles.
Figure 2B:
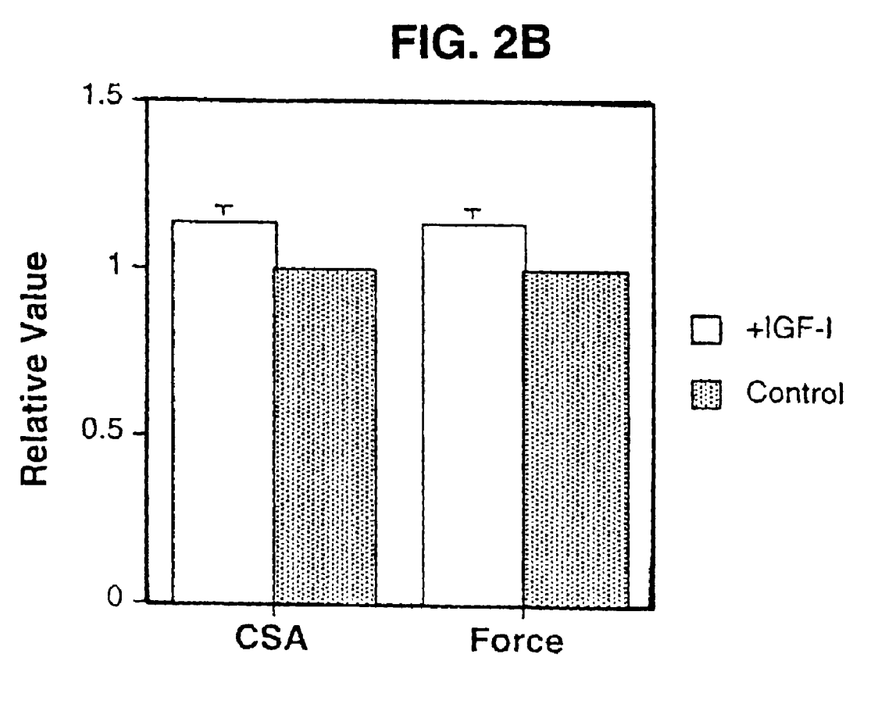

The effects of this IGF-I expression on muscle morphology are demonstrated in FIG. 2A in hematoxylin and eosin stained muscle cross sections. In young adult mice (examined at 6 months of age following rAAV-IGF-I injection at 2 months of age), the average mass of the extensor digitorum longus (EDL) muscle increased by 15%. Further, central nuclei were visible in the muscle fibers which is indicative of ongoing regeneration (Carlson et al., 1983, Med. Sci. Sports Exerc. 15:187–198). Additionally, the presence of neonatal myosin in rAAV-IGF-I-injected muscles provides further evidence of regeneration since developmental expression of myosin has also been demonstrated to accompany regeneration. Indeed, Sartore et al. (1982, Nature 298:294–296), demonstrated that when satellite cells are activated and fuse with existing muscle fibers, their nuclei recapitulate the progression through the series of developmental myosin heavy chain isoforms. Thus, expression of developmental myosin heavy chain isoforms further confirms satellite cell activation and muscle regeneration in rAAV-IGF-I-injected muscles.

Figure 3A:
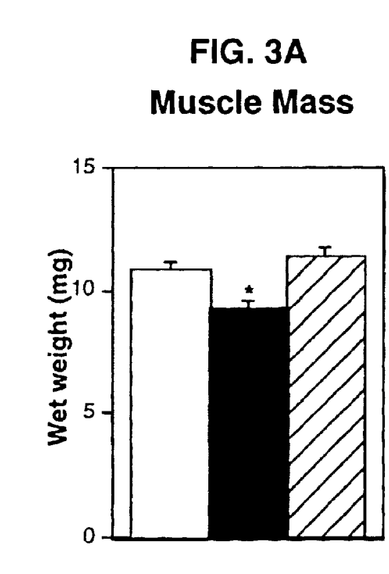
FIG. 3, comprising three panels, is a series of graphs depicting the effect of IGF-I expression in EDL muscles of old (27-month) mice compared to control non-injected young (6-month) mice and old (27-month) mice EDLs. Left panel: This graph depicts (from left to right) the muscle mass (wet weight) of young, control EDL; old, control EDL; and rAAV-IGF-injected old EDL, respectively. Middle panel: This graph depicts (from left to right) the tetanic force of young control EDL, old control EDL, and rAAV-IGF-I-injected old EDL, respectively. Right panel: This graph depicts (from left to right) the specific force of young control EDL, old control EDL, and rAAV-IGF-I-injected old EDL, respectively. For determination of specific force, the cross-sectional area of the EDL muscle was estimated using muscle mass and optimum muscle length pursuant to Brooks and Faulkner (1988, J. Physiol. 404:71–82). The symbol "*" denotes p<0.05 for comparisons to young adult control muscles.
Figure 3B:
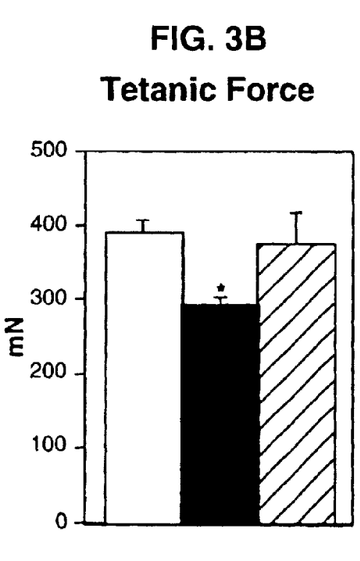
Figure 3C:
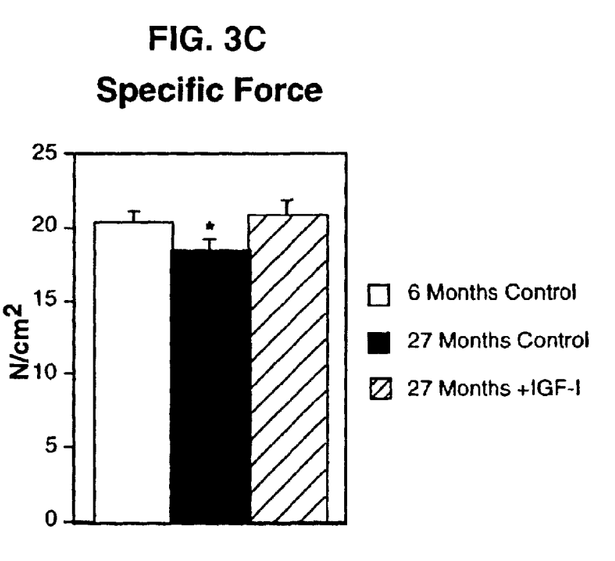

In the case of the old mice examined at 27 months of age following rAAV-IGF-I injection at either 18 or 24 months of age, the muscle mass increased 19% compared with control non-injected muscle. Thus, the normal decrease of muscle mass associated with aging (15% in mice) was completely prevented by viral administration of IGF-I (FIG. 3). Moreover, similar to the situation observed in the young animals, central nuclei were evident in muscle cells at 4 months following viral injection in the old animals. However, at 9 months following injection, no central nuclei were observed even though IGF-I expression was maintained (FIG. 1B). This suggests that the muscles eventually reach a new steady state in which regeneration is no longer evident.

From a functional standpoint, the effects of the viral IGF-I expression were even more surprising in extent. In the young animals injected with rAAV-IGF-I, the increase in overall muscle mass and in the muscle cross-sectional area translates into increased force production (isometric force increased by 15%), without any changes in muscle fiber number (control 726±54; +rAAV-IGF-I:785±96), fiber types, or any other contractile parameters. Therefore, these data disclose that hypertrophy of individual fibers has been induced with concomitant increase in force, a result never achieved before in the prior art.

In the old animals, the functional results of IGF-I expression mediated by rAAV-IGF-I injection were even more remarkable. rAAV-IGF-I-injected old mouse muscles demonstrated increased force that was greater than the increase observed in the muscle cross-sectional area (27% increase in force vs. 15% increase in cross-sectional area). Thus, a hallmark of aging skeletal muscle, i.e., reduction in the specific force of muscle (which is defined as the force per cross-sectional area), has been prevented by rAAV-IGF-I injection (FIG. 3).

Furthermore, the uninjected, control old EDL muscles exhibited a significant selective loss of the fastest, most powerful fiber types, the IIb fibers (a 24% decrease), which is another hallmark of aging skeletal muscle. However, another remarkable feature of rAAV-IGF-I injection is that it completely prevented this selective fiber type loss. More specifically, the muscle fiber type make-up of uninjected young animals (64% IIb) and in rAAV-IGF-I-injected young animals (65% IIb) was similar to that in rAAV-IGF-I-injected old animals (69% IIb) which are all much higher than the 45% IIb demonstrated in uninjected old animals. Therefore, rAAV-IGF-I injection prevents the selective loss of the powerful type IIb muscle fibers in old animals.

The effects of the IGF-I production were local. That is, average circulating IGF-I levels were not elevated (248±19.5 ng/ml plasma for control; 217±46.5 ng/ml plasma for rAAV-IGF-I-injected), and the muscles of contralateral limbs of animals receiving single limb injections were indistinguishable from muscles of uninjected animals. This is important because elevation of IGF-I levels in the blood could lead to undesirable deleterious effects in other tissues (Stewart et al., 1996, Physiol. Reviews 76:1005–1026). The mechanism by which IGF-I is restricted to the injected muscle is unclear. Without wishing to be bound by theory, it may be that the muscle extracellular matrix traps secreted IGF-I, or that IGF-I is incapable of gaining access to the blood if secreted from muscle. On the other hand, past failures of increased circulating levels of IGF-I to markedly improve muscle function despite increasing muscle mass (Papadakis et al., 1996, Ann. Intern. Med. 124:708–716), may have resulted either from an inability to sufficiently elevate local concentrations of IGF-I in muscle or from a failure of the circulating IGF-I to gain access into and to activate satellite cells.

The present invention suggests that the mechanism by which the viral-mediated muscle fiber secretion of IGF-I prevents aging-related loss of function is, at least in part (beyond its general anabolic effects), through the activation of satellite cells which leads to increased muscle regeneration. During muscle regeneration, IGF-I levels have been shown to increase (Krishan et al., 1996, J. Muscle Res. and Cell Motility 17:513–521). Additionally, it is known that addition of IGF-I activates satellite cells in culture, increasing the rate of cellular proliferation and formation of myotubes, ultimately resulting in hypertrophied myotubes (Allen et al., 1989, J. Cell Physiol. 138:311–314). In mice in which satellite cells have been destroyed by irradiation, muscles fail to hypertrophy in response to chronic overload, suggesting that activation of satellite cells is essential for normal hypertrophy (Rosenblatt et al., 1992, J. Appl. Physiol. 73:253–257). That IGF-I-induced satellite cell activation in the experiments described herein is supported by the appearance of central nuclei and developmental myosin heavy chain expression 4 months post-injection of virus. Furthermore, the DNA content of the muscles (Labarca et al., 1980, Anal. Biochem. 102:344–352) increased in excess of the increase in muscle mass (28% increase in DNA content vs. 15% increase in mass). The outcome is preservation of both muscle strength and mass, and prevention of loss of the fastest fiber types (IIb). Based on these results, and without wishing to be bound by theory, it may be that the primary cause of the aging-related loss in strength that precedes, and is in excess of, the loss of muscle mass, is a failure to activate satellite cells in order to repair cumulative injury that results from normal muscle utilization.

EXAMPLE 2

Generation of Transgenic Animals Comprising and Expressing an IGF-I Isolated Nucleic Acid Transgenic mice were generated which comprise the same MLC-IGF expression cassette as that included in the AAV-IGF construct described herein (excluding the viral ITRs). These mice were generated to test the hypothesis that enhanced IGF-I expression would induce skeletal muscle hypertrophy and result in an increase in muscle mass in juvenile and adult animals. The generation of such animals has obvious applications for meat producing vertebrates, including fish, birds, cows, sheep, pigs, etc. Previous work has demonstrated that the MLC regulatory elements included in the transgene results in gene expression as early as E9.5 in mouse embryogenesis, and remain highly active in fast fibers, with the highest expression in type IIb fibers.

Three established lines of mice having the MLC-IGF transgene were found to express high levels of transgenic IGF-I in fast skeletal muscle. These animals exhibited normal muscle morphology at birth, but by 5 weeks after birth they displayed marked skeletal muscle hypertrophy compared to non-transgenic mice. Histological analysis of transgenic muscle revealed that fast fibers were approximately 50% larger in cross section than those obtained from wild type animals. This change in relative fast fiber size was also accompanied by an overall shift in fiber composition towards a faster fiber type. Immunocytochemical analysis revealed a predominance of fast Type IIb fibers in the transgenic as compared with wild type muscle, indicating either that Type IIb fibers were preferentially favored early during fiber type diversification or that other fiber types had been transformed into Type IIb by forced IGF-I expression.

Figure 5A:
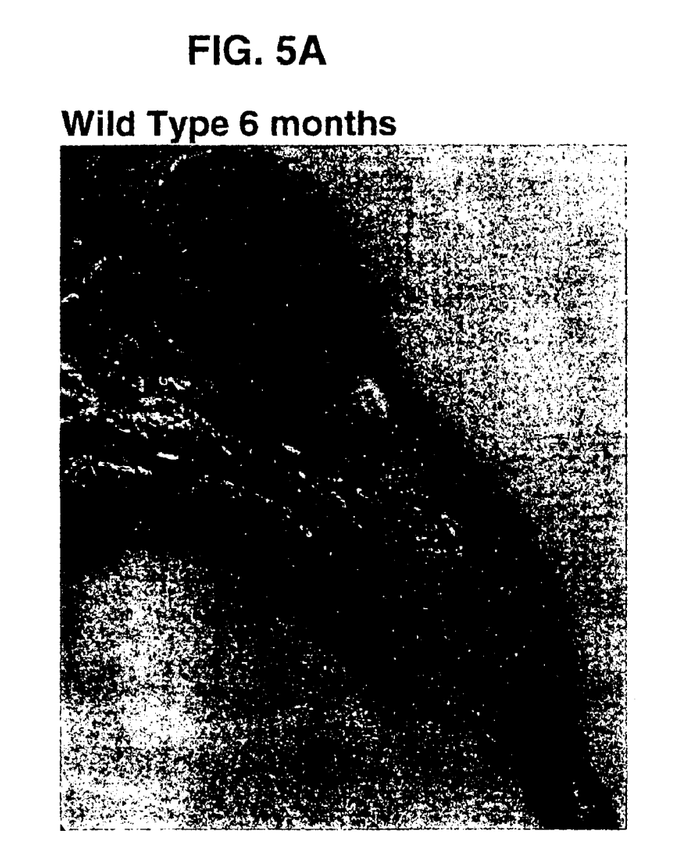
FIG. 5 is an image of the muscles of a transgenic mouse having the MLC/IGF-I construct, compared with the muscles of an otherwise identical non-transgenic mouse.
Figure 5B:
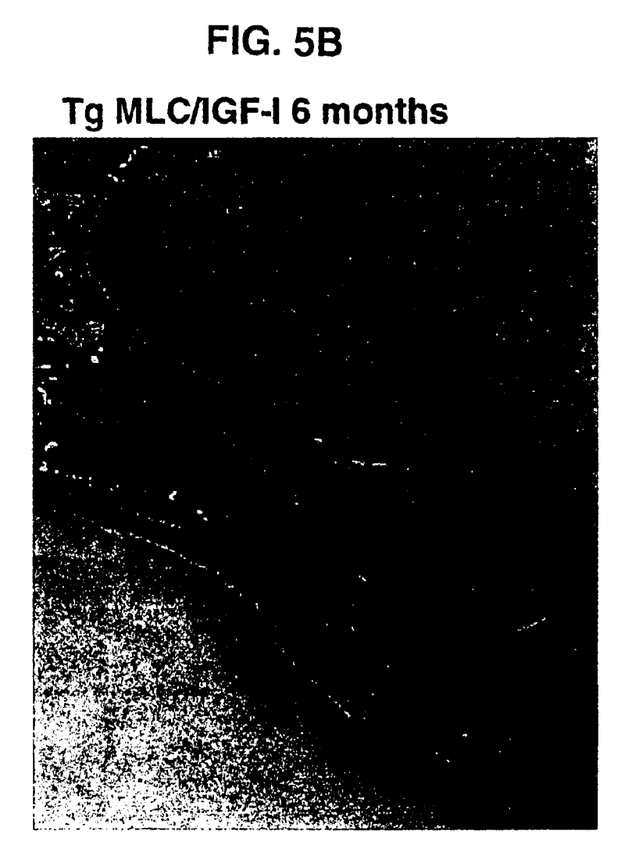

In addition, primary myoblasts isolated from transgenic 2 week old animals displayed a precocious differentiation and subsequent hypertrophy compared to wild type cultures, suggesting that IGF-I potentiates and accelerates the myogenic program in satellite cells derived from these animals. Such a pattern should be reproduced in all other vertebrates expressing the transgene, and will lead to the production of animals that will be born without complication (animal size essentially normal at birth), and will have an increased mass of muscle for meat production in juvenile and adult stages of life. An illustration of the muscles of transgenic mice, compared with otherwise identical non-transgenic mice, is shown in FIG. 5.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid comprising a vertebrate Insulin-like Growth Factor I (IGF-I) coding region, operably linked to a muscle specific promoter/regulatory region, wherein said IGF-I coding region is flanked on the 5' side by an SV40 intron sequence and wherein said IGF-I coding region is flanked on the 3' end by an SV40 polyadenylation signal sequence.

2. The isolated nucleic acid of claim 1, wherein said muscle specific promoter/regulatory region is selected from the group consisting of the myosin light chain 1/3 promoter/enhancer, the skeletal α-actin promoter, the muscle creatine kinase promoter/enhancer and a muscle specific troponin promoter.

3. The isolated nucleic acid of claim 2, wherein said muscle specific troponin promoter is the fast troponin C promoter/enhancer.

4. The isolated nucleic acid of claim 2, wherein said muscle specific promoter/regulatory region is the myosin light chain 1/3 promoter/enhancer.

5. The isolated nucleic acid of claim 1, wherein said muscle specific promoter/regulatory region further comprises an enhancer element operably linked to the IGF-I coding region.

6. The isolated nucleic acid of claim 5, wherein said enhancer is the myosin light chain 1/3 enhancer.

7. A composition comprising a recombinant virus vector comprising the isolated nucleic acid of claim 6.

8. The composition of claim 7, wherein said recombinant virus vector is selected from the group consisting of an adeno-associated virus, an adenovirus and a herpes simplex virus.

9. The composition of claim 8, wherein said recombinant virus vector is an adeno-associated virus.

10. A cell comprising the isolated nucleic acid of claim 1.

11. A cell comprising the recombinant virus vector of claim 9.

12. A kit for increasing muscle mass and muscle strength in a vertebrate, said kit comprising a muscle enhancing dose of the isolated nucleic acid encoding IGF-I of claim 1, wherein said isolated nucleic acid is expressed in vertebrate muscle cells, and wherein said kit further comprises an applicator for delivering said muscle enhancing dose, and instructions for the use of said kit.

13. A method of increasing vertebrate muscle mass and muscle strength, said method comprising administering a muscle enhancing dose of an isolated nucleic acid encoding Insulin-like Growth Factor I (IGF-I) intramuscularly into a vertebrate, wherein said isolated nucleic acid is expressed in muscle cells, thereby increasing said muscle mass and said muscle strength in said vertebrate, wherein said method further comprising administering to said vertebrate fibroblast growth factor or neurotropin.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: RAT

<400> SEQUENCE: 1
tgctcacctt taccagctcg g                                              21

<210> SEQ ID NO 2
<211> LENGTH: 22
<212> TYPE: DNA
<213> ORGANISM: RAT

<400> SEQUENCE: 2
gcccggatgg aacgagctga ct                                             22

<210> SEQ ID NO 3
<211> LENGTH: 1052
<212> TYPE: DNA
<213> ORGANISM: RAT

<400> SEQUENCE: 3
ggacgtacca aaatgagcgc acctccaata aagatacaca tcatgtcgtc ttcacatctc     60
ttctacctgg cactctgctt gctcaccttt accagctcgg ccacagccgg accagagacc    120
ctttgcgggg ctgagctggt ggacgctctt cagttcgtgt gtggaccaag gggcttttac    180
ttcaacaagc ccacaggcta tggctccagc attcggaggg caccacagac gggcattgtg    240
gatgagtgtt gcttccggag ctgtgatctg aggaggctgg agatgtactg tgctccgctg    300
aagcctacaa agtcagctcg ttccatccgg gcccagcgcc acactgacat gcccaagact    360
cagaaggaag tacacttgaa gaacacaagt agaggaagtg caggaaacaa gacctacaga    420
atgtaggagg agcctcccga ggaacagaaa atgccacgtc accgcaagat cctttgctgc    480
```

-continued

```
ttgagcaacc tgcaaaacat cggaacacct gccaaatatc aataatgagt tcaataccat    540
ttcagagatg ggcatttccc tcaatgaaat acacaagtaa acattccgac attgtcttta    600
ggagtggttt gttaaaaaaa aaacaaaaa acaaaaacaa aaacaaaaaa aaagcttgca    660
ccttgcaaaa gtggtcctgg cgtgggtaga ttgctgttaa tcctttatca ataacgttct    720
atagagaata tataaatata tatataatta tatctcctag tccctgcctc ttaagagccg    780
aaaatgcatg ggtgttgtag acattcggtt gcactaaatt cctctctgaa ttttggctgc    840
tgaagccgtt catttagcaa ctgtttatag gtggttgatg aatggttcct tatctccatt    900
tcttcctatg tagcttaagc cgcttccttc acagaatcta ataatctcgt ctaggccatt    960
agccctgccc tttcttaaca ttcttgtatt tgttgaattt ggcctcctcg aaagcaatag   1020
caactgggtg gcccacccaa gttttaacgc cc                                 1052
```